US009492649B2

(12) United States Patent
Carrez et al.

(10) Patent No.: US 9,492,649 B2
(45) Date of Patent: Nov. 15, 2016

(54) SET OF EASILY CLEANABLE CONNECTORS FOR A LIQUID CIRCUIT

(75) Inventors: Jean-Luc Carrez, Ecouen (FR); Pierrick Guyomarc'h, Ermont (FR)

(73) Assignee: Vygon (FR)

( * ) Notice: Subject to any disclaimer, the term of this patent is extended or adjusted under 35 U.S.C. 154(b) by 1036 days.

(21) Appl. No.: 13/579,324

(22) PCT Filed: Feb. 16, 2011

(86) PCT No.: PCT/EP2011/052315
§ 371 (c)(1),
(2), (4) Date: Aug. 16, 2012

(87) PCT Pub. No.: WO2011/101389
PCT Pub. Date: Aug. 25, 2011

(65) Prior Publication Data
US 2012/0316536 A1    Dec. 13, 2012

(30) Foreign Application Priority Data

Feb. 17, 2010  (FR) .................................. 10 51136
Jun. 9, 2010   (FR) .................................. 10 54539

(51) Int. Cl.
*A61M 39/00*    (2006.01)
*A61M 39/26*    (2006.01)
*A61M 39/10*    (2006.01)

(52) U.S. Cl.
CPC .......... *A61M 39/26* (2013.01); *A61M 39/1011* (2013.01); *A61M 2039/267* (2013.01)

(58) Field of Classification Search
CPC ........... A61M 39/26; A61M 39/1011; A61M 39/10; A61M 2039/267; A61M 2039/1027; A61M 2039/1033; A61M 2039/1077; A61M 39/12; A61M 25/0014; A61M 5/14276; A61M 39/14; A61M 39/16; A61M 2039/009
USPC ................................. 604/533–537
See application file for complete search history.

(56) References Cited

U.S. PATENT DOCUMENTS

| | | | | |
|---|---|---|---|---|
| 4,360,024 | A | * | 11/1982 | Wallace ..................... 604/256 |
| 5,492,147 | A | * | 2/1996 | Challender .......... F16L 29/005 137/614.05 |
| 2005/0090805 | A1 | * | 4/2005 | Shaw et al. .................... 604/523 |
| 2006/0157971 | A1 | * | 7/2006 | Baldwin .............. A61M 39/26 285/3 |
| 2007/0017583 | A1 | * | 1/2007 | Fangrow, Jr. ......... A61M 39/10 137/614.06 |

FOREIGN PATENT DOCUMENTS

EP    0544581 A1    6/1993
FR    2929123    * 10/2009
(Continued)

OTHER PUBLICATIONS

French Search Report for Application No. FR1054539 dated Sep. 22, 2010.
(Continued)

*Primary Examiner* — Bhisma Mehta
*Assistant Examiner* — Bradley G Thomas, Jr.
(74) *Attorney, Agent, or Firm* — Lerner, David, Littenberg, Krumholz & Mentlik, LLP (57) ABSTRACT

The invention relates to a secure connector set for a liquid circuit, including: a male connector and a female connector, each including a proximal coupler and a distal coupler, the distal coupler of each connector defining a passage and including a tubular part, in which a connection member fixedly mounted on the proximal coupler extends coaxially, and an elastically deformable membrane which is substantially tubular, closed at a distal end by a membrane body, and movable between a downstream plugging position, in which the membrane sealingly covers a free end of the connection member, and an upstream connection position, in which the connection member passes through the membrane, in which the tubular part of the distal coupler of the male connector is designed to be inserted, upon connection, into the tubular part of the distal coupler of the female connector, and wherein, in a downstream plugging position, for the male and the female connectors, the membrane sealingly blocks the passage in the distal coupler.

14 Claims, 7 Drawing Sheets

FOREIGN PATENT DOCUMENTS

| | | | |
|---|---|---|---|
| FR | 2929123 | A1 | 10/2009 |
| FR | 2931363 | A1 | 11/2009 |
| WO | 2006076656 | A2 | 7/2006 |
| WO | 2006078355 | A1 | 7/2006 |

OTHER PUBLICATIONS

International Search Report for Application No. PCT/EP2011/052315 dated May 12, 2011.

* cited by examiner

SET OF EASILY CLEANABLE CONNECTORS FOR A LIQUID CIRCUIT

CROSS REFERENCE TO RELATED APPLICATIONS

The present application is a national phase entry under 35 U.S.C. §371 of International Application No. PCT/EP2011/052315 filed on Feb. 16, 2011, which claims priority from French Application No. 1051136, filed Feb. 17, 2010 and French Application No. 1054539, filed Jun. 9, 2010, the disclosures of which are incorporated by reference herein.

FIELD OF THE INVENTION

The invention relates to a connector for a liquid circuit, especially for medical use.

BACKGROUND OF THE INVENTION

Document EP 0 544 581 discloses such a secure connector comprising a distal entry cone of female Luer type designed to be connected to a device having a connector of compatible and complementary male Luer type. The distal entry cone is blocked by a septum or membrane having a flush surface which is easily cleaned for removal of germs or bacteria before eventual connection is made. The septum protects a tube which, once the connection is made, extends in part in the hole of the connector of male Luer type to which it is connected. Once connected, the connector of document EP 0 544 581 presents a straight tubular passage and reduced dead volume. Document EP 0 544 581 describes a secure female connector.

However, it becomes necessary to have a male connector having the same properties to benefit from the same security of use as the female connector of document EP 0 544 581. In addition, in cooperation with the connector of document EP 0 544 581, use of such a secure male connector would produce a secure universal connection.

French patent application FR 2 931 363 has therefore proposed a connector for a liquid circuit, especially for medical use, comprising a proximal coupler, a distal coupler defining a passage, a hollow tube mounted fixed on the proximal coupler, extending in the passage of the distal coupler and comprising a free distal end, and an elastically deformable membrane, substantially tubular, closed at a distal end by a membrane thickness and designed to cover the free end of the hollow tube substantially tightly at rest, the distal coupler being mounted to slide relative to the proximal coupler between a distal rest position and a proximal position of use in which the hollow tube can be selectively disengaged from said membrane thickness.

The use of such a distal coupler mounted to slide relative to the proximal coupler especially disengages the free distal end from the hollow tube protected by the membrane for cleaning of the latter to remove all germs or bacteria prior to connection, the hollow tube playing the role of male part of the connector.

However, the applicant has realised that the male and female connectors were difficult to clean, especially at the level of their respective distal parts comprising the membrane. Now, especially in the domain of chemotherapy where drugs are very aggressive during their preparation by personnel or when injected into patients, the property of the material used is fundamental to the extent where patients are very sensitive to nosocomial diseases.

Also, connection and disconnection of the set of connectors is difficult and requires several steps on the part of the operator.

Finally, current locking means do not guarantee the user that the connectors are effectively properly connected. In particular, when threadings are used at the level of the ends of the male and female connectors to be connected, the operator often cannot know if he has sufficiently screwed the connectors together and if the connection of the tubes has been completed correctly.

BRIEF SUMMARY OF THE INVENTION

The aim of the invention therefore is to propose an improved male and female connection.

For this, the invention proposes a secure connection set for a liquid circuit, comprising:
a male connector and a female connector, each comprising a proximal coupler and a distal coupler,
the distal coupler of each of the connectors defining a passage and comprising a tubular part, in which a connection element mounted fixed on the proximal coupler extends coaxially, and an elastically deformable membrane, substantially tubular, closed at a distal end by a membrane thickness and mobile between a downstream blocking position, in which the membrane tightly covers a free end of the connection element, and an upstream connection position, in which the connection element passes through the membrane,
in which the tubular part of the distal coupler of the male connector is adapted to be inserted, during connection, into the tubular part of the distal coupler of the female connector, and in that, in a downstream blocking position, for each of the male and female connectors the membrane sealingly blocks the passage of the distal coupler.

Some preferred, though non-limiting, aspects of the connection set according to the invention are the following:
the external surface of the tubular part of the female connector is devoid of threading,
the external surface of the tubular part of the male connector comprises threading so as to constitute a connectable entry of "Luer-Lock" type,
the male connection element and the female connection element are hollow tubes, and in that the hollow tube of the male connector is adapted to be inserted into the hollow tube of the female connector,
the external surface of the tubular part of the distal coupler of each male connector and female is smooth and has an unvarying axial cross-section over a substantially continuous part and comprises holding means extending transversally, said surface and said holding means forming male locking means or female,
the holding means of the male locking means comprises at least one pin extending transversally from the smooth surface relative to the longitudinal axis of the coupler,
the male locking means comprise two pins extending on either side of the coupler, in opposite directions,
the holding means of the female locking means comprise at least one groove formed in the surface of a collar and designed to receive the pin of the male locking means,
the groove is bent,
the collar extends over part of the coupler only,
the threadings extend over the surface of the tube which is not covered by the collar,
the collar is open-work at the level of a proximal end, the membrane comprises a slot in the membrane thickness arranged such so as to be passed through by the connection element in an upstream connection position.

According to a second aspect, the invention proposes the use of a set of a male connector and a female connector described herein, comprising the steps consisting of:
cleaning the membrane;
putting in place the proximal ends of the male and female connectors, such that their respective membranes are in contact and the two connectors have their longitudinal axes joined to create a tight seal of the two connectors;
inserting the male connector into the female connector such that the connection element of the male connector is connected in the connection element of the female connector; and
locking the assembly.

The connector for a liquid circuit, especially for medical use, and having a longitudinal axis, comprises:
a proximal coupler;
a distal coupler defining a passage extending along the longitudinal axis;
a hollow tube mounted fixed on the proximal coupler, extending in the passage of the distal coupler and comprising a free distal end; and
an elastically deformable membrane, substantially tubular, closed at a distal end by a membrane thickness and designed to cover the free end of the hollow tube substantially tightly at rest,
in which the surface of the distal coupler is smooth and of unvarying axial cross-section over a substantially continuous part of the distal coupler and comprises holding means extending transversally, said smooth surface and said holding means forming male or female locking means.

Some preferred, though non-limiting, aspects of this connector are the following:
the holding means of the male locking means comprise at least one pin extending transversally from the smooth surface relative to the longitudinal axis of the distal coupler;
the male locking means comprise two pins extending on either side of the distal coupler, in opposite directions;
the holding means of the female locking means comprise at least one groove formed in the surface of a collar and designed to receive the pin of the male locking means;
the groove is bent;
the end of the groove serving as stop for the pin comprises a recess forming a restraint for the pin in a locked position;
the collar extends over part of the distal coupler only; and
a central part of the distal coupler not covered by the collar comprises threadings so as to constitute a connectable entry of "Luer-Lock" type.

A set of at least two connectors in keeping with the above, designed to cooperate together to create a circuit for fluids, especially in the medical domain, presents the fact that the locking means of one of the connectors are male, and the locking means of the other of the connectors are female.

Some preferred, though non-limiting, aspects of such a set are the following:
one of the locking means comprises at least one pin extending transversally from the smooth surface relative to the longitudinal axis of the distal coupler; and
the other of the locking means comprises a smooth surface (260) in which at least one groove bent designed to receive the pin of the first locking means is formed the smooth surface from which the pin extends is the external surface of the distal coupler of the male locking means; and
the smooth surface in which the groove is formed is the internal surface of a collar, arranged on the distal end of the female locking means;
the width of the groove is substantially equal to the diameter of the pin taken in a direction transversal to a direction of insertion of the pin in the groove, and the length of the groove is substantially equal to the relative distance traversed by the connectors when they are coupled; and
the distal couplers of the two connectors are structurally similar, outside of their respective locking means, their respective membranes flush with the distal ends of said distal couplers such that coupling/uncoupling of the male connector and of the female connector is completed in a single axial movement.

Use of such a set comprises the steps consisting of:
cleaning the membrane and the respective locking means of the connectors;
putting in place the distal ends of the connectors such that their respective membranes are in contact and the two connectors have their longitudinal axes joined, to produce a tight seal of the two connectors;
angularly positioning the connectors such that the at least one pin is placed in the longitudinal axis of the corresponding groove;
supporting the two connectors against each other until the pin abuts against the end of the groove; and
turning the connectors relatively one relative to the other so as to lock the pin in the groove.

BRIEF DESCRIPTION OF THE DRAWINGS

Other characteristics, aims and advantages of the present invention will emerge more clearly from the following detailed description, and with reference to the attached diagrams given by way of non-limiting examples and in which:

FIG. 6 is a sectional view of the set of FIG. 5a.

DETAILED DESCRIPTION

In reference to FIGS. 1 to 2, a female connector 100 according to the invention will now be described.

The female connector 100 comprises a proximal coupler 120, an elastically deformable membrane 130, substantially tubular, and a distal coupler 140.

The proximal coupler 120 is of generally tubular in shape and comprises a proximal end which here comprises a connectable entry 121 of female "Luer-Lock" type. By way of variant embodiment, this connectable entry 121 is of "Luer-Lock" type male. It is extended in a distal direction by a hollow body 122 which comprises near the proximal end an annular bulge 126 projecting and extending on a radially external circumference of the hollow body 122 of the proximal coupler 120, designed to cooperate with a complementary annular groove 142 provided on the distal coupler 140, to block the proximal 120 and distal 140 couplers in translation one relative to the other, as will be explained hereinbelow. The hollow body 122 of the proximal coupler 120 terminates, in a distal direction, by a rim 123 of circular shape surmounted coaxially by a hollow tube 124 which projects from the proximal coupler 120 in a distal direction. The hollow tube 124 terminates by a free distal end 125. The hollow tube forms a connection element. The distal coupler 140 has a tubular shape and defines a passage 141.

As a variant, the proximal coupler 120 comprises at least one picot, preferably two, which cooperates with as many orifices provided on the distal coupler 140.

The membrane 130 of the connector 100 will now be described in greater detail.

This membrane 130 comprises elastic means 131, here a spring 131, for example of helicoidal compression spring type, forming a membrane body, extending as far as a distal end 132 closed by a membrane thickness. These elastic means 131 are designed to bear on the proximal coupler 120 and thrust the distal end 132 of the membrane such that the latter reaches a stable downstream blocking position of a distal end of the passage 141.

By way of variant, the body of the membrane 130 is undulating, and is in the form of bellows.

A slot 133 passing through said membrane thickness is made in this membrane thickness.

Optionally, on a radially external circumference the distal end 132 of the membrane 130 has a groove designed to receive reinforcement/constriction means 134, here in the form of a cup which encloses the slot 133 and, in a rest position, ensures that the latter is closed tightly to prevent any loss of pressurised fluid which might be present in the hollow tube 124 during use of the connector 100 mounted on a fluid circuit.

Figure 1:
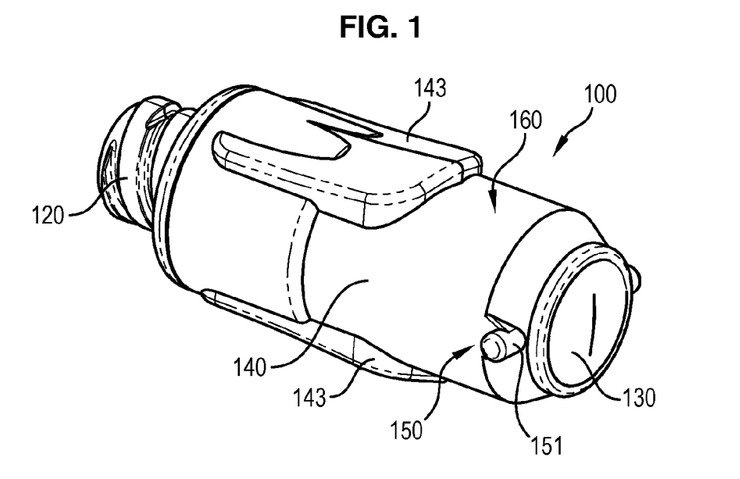
FIG. 1 is a three-dimensional view off a connector comprising male locking means according to the invention, at rest.
Figure 2:
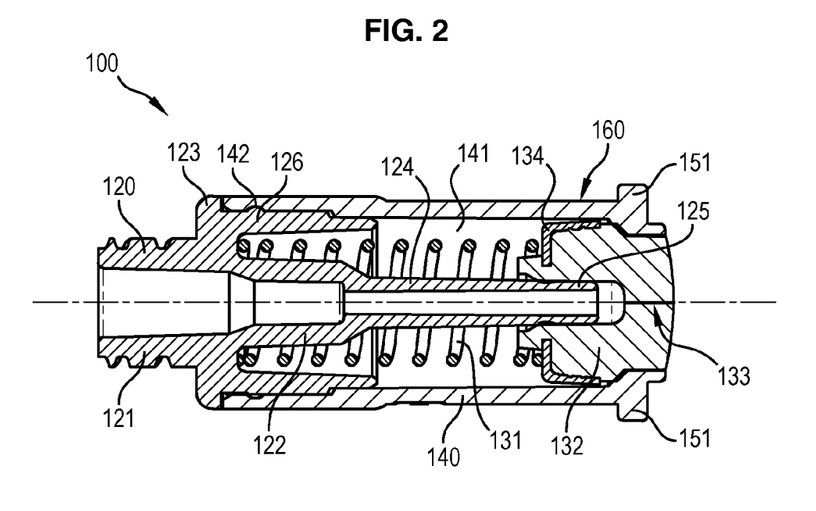
FIG. 2 is a sectional view of the connector of FIG. 1.
Figure 3A:
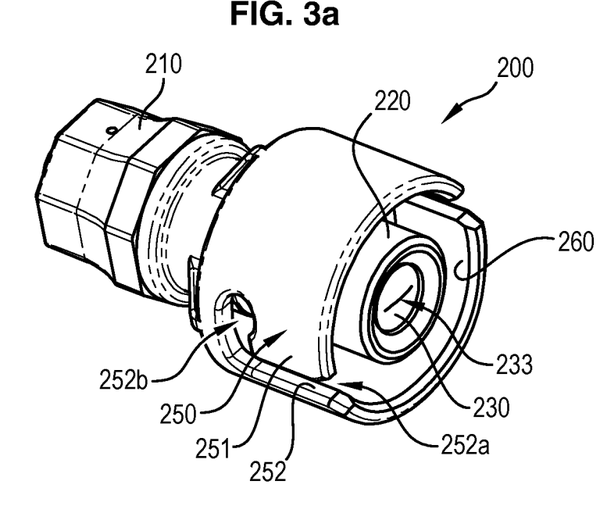
FIGS. 3a and 3b are three-dimensional views of two embodiments of a connector comprising female locking means according to the invention, at rest.
Figure 3B:
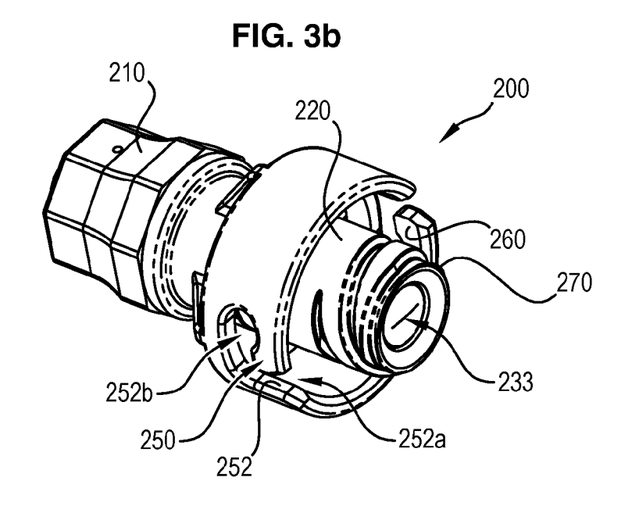
Figure 4A:
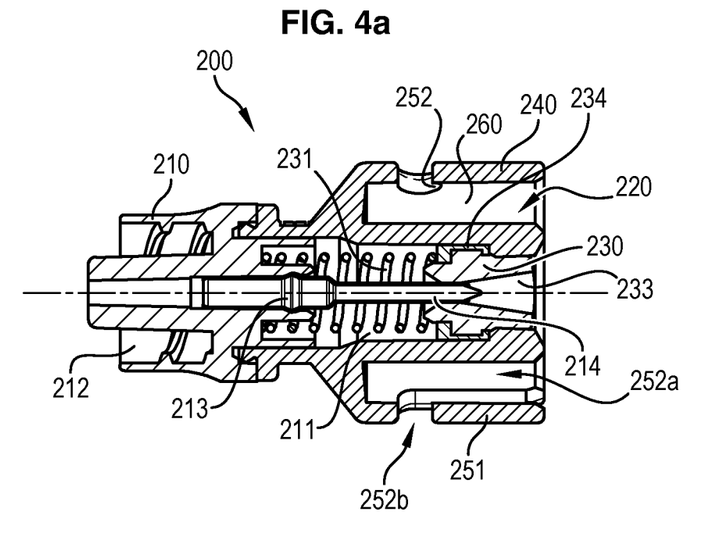
FIGS. 4a and 4b are sectional views of the connectors of FIGS. 3a and 3b respectively, at rest.
Figure 4B:
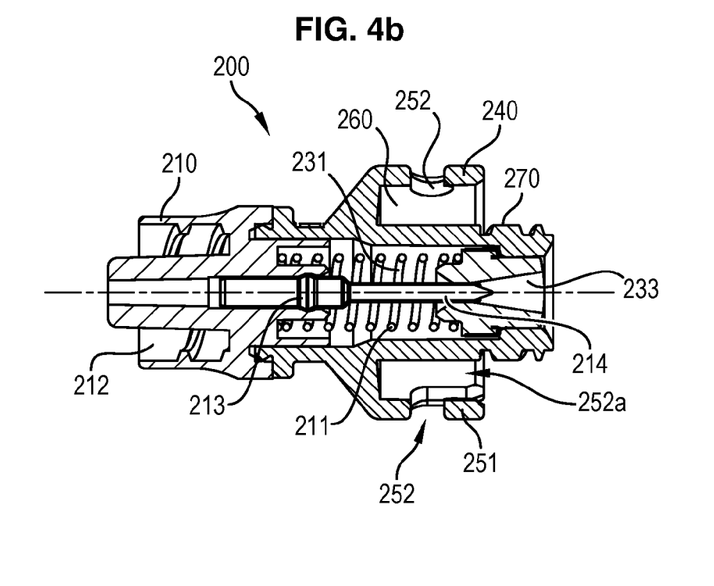

In addition, the particular form of the body 131 of the membrane 130 enables the latter to be able to deform elastically in a longitudinal direction and to act as recoil spring allowing the membrane 130 to resume its initial rest form, such as illustrated in FIGS. 1 and 2, during disconnection of the connector 100.

The female connector 100 accordingly comprises a membrane 130 which is encapsulated in the tubular part of the distal coupler 140. In a stable downstream blocking position this also allows radial clamping of the membrane 130, and in particular of the distal end 132 of the latter, made by a wall of the tubular part of the distal coupler 140: this results in better sealing and improved resistance to pressure.

The membrane 130 is made of elastomer material, such as polyisoprene, silicone, or thermoplastic elastomer (TPE).

During mounting, the spring 131 forming the body of the membrane 130 is threaded onto the hollow tube 124 of the proximal coupler 120.

On its periphery, preferably in the proximal part, the distal coupler 140 comprises male or female locking means 150. These locking means 150 will be detailed hereinbelow in the description.

The distal coupler 140 also comprises handling means 143 of the connector 100. Here, there are two of them and project radially and centrifugally on either side of the distal coupler 140. These handling means 143 firmly hold the connector 100 during its connection with a male connector.

During mounting, the distal coupler 140 is mounted on the proximal coupler 120 such that the annular projection 126 is positioned in the corresponding annular groove 142. The distal coupler 140 is then fixed according to usual processes on the proximal coupler 120, for example by adhesion of their respective contact surfaces to produce a monobloc casing, or by ultrasound welding.

A male connector 200 according to the invention will now be described.

In reference to FIGS. 3a, 3b, 4a and 4b, a male connector 200 comprises a proximal coupler 210 and a casing 220 mounted on the proximal coupler 210. Assembly of the casing 220 on the proximal coupler 210 delimits a substantially tubular chamber 211 forming a passage. The proximal coupler 210 comprises a connectable entry 212, here, of male "Luer-Lock" type. By way of variant embodiment, this connectable entry 212 is of female "Luer-Lock" type. Nested in this proximal coupler 210, the connector 200 comprises a connection element 213, here in the form of a hollow tube 213 extending into the passage substantially tubular 211 in a distal direction.

The casing 220 is formed by a distal coupler 240 and comprises a tubular part.

The proximal coupler comprises a membrane or septum 230 which comprises a slot 233 in its thickness. The slot 233 is substantially perpendicular to a longitudinal axis of the connector 200.

The connector 200 finally comprises elastic means 231, here a spring 231, for example of helicoidal compression spring type, but which can also take any other shape known to the expert. The spring 231 is designed to be supported on the proximal coupler 210 and to thrust the septum 230 so that the latter reaches a stable downstream blocking position of a distal end of the passage 211.

A more detailed description of a connector similar to the connector 200 is provided in document EP 0 544 581 which can be referred to for this purpose.

The septum 230 is here an elastomer membrane of general cylindrical shape in revolution comprising a substantially plane slot 233 perpendicular to a longitudinal axis of the septum 230. This slot 233 extends from a downstream surface as far as into an upstream opening of substantially cylindrical shape in revolution designed to tightly receive a free end of the hollow tube 214.

The septum 230 is mounted in a rigid cup 234 forming reinforcement/constriction means. By way of variant embodiment, this cup is surmounted by an elastically deformable ring, forming part of reinforcement/constriction means.

A more detailed description of the reinforcement/constriction means 234 is provided in document FR 2 929 123 which can be referred to for this purpose.

In this way, the male connector 200 comprises a septum (or membrane) 230 which is encapsulated in the tubular part of the distal coupler 240. In a stable downstream blocking position this also allows radial clamping of the septum 230, and in particular at the level of the slot 233 of the latter, made by a wall of the tubular part of the distal coupler 240: this results in better sealing and improved resistance to pressure.

On its periphery, preferably at the level of a distal end, the distal coupler 240 comprises female or male locking means 250.

Throughout the description, the embodiment according to which the female connector 100 comprises male bayonet locking means, whereas the male connector 200 comprises female bayonet-locking means will be described in greater detail. This is in no way limiting, to the extent where the embodiment consisting of providing female locking means on the female connector 100 and male locking means on the male connector 200 is equivalent and also covered by the invention.

The locking means 250 of the male connector 200 is preferably complementary to the locking means 150 of the female connector 100.

According to the invention, when the locking means 250 are female, they are formed by a smooth surface 260 having a unvarying axial cross-section over part substantially continue of the distal coupler 240, and a holding means 252 extending transversally.

The male locking means 150 are also constituted by a smooth surface 160 and having holding means 151 extending transversally, of a shape complementary to the shapes of the smooth surface 260 and of the holding means 252 of the female locking means 250 respectively.

Such an embodiment therefore makes cleaning of the locking means easier, to the extent where it reduces projecting edges on the surfaces 160, 260 to be cleaned, by opposition to the locking means by threading, which has wide use in the prior art.

Figure 9:
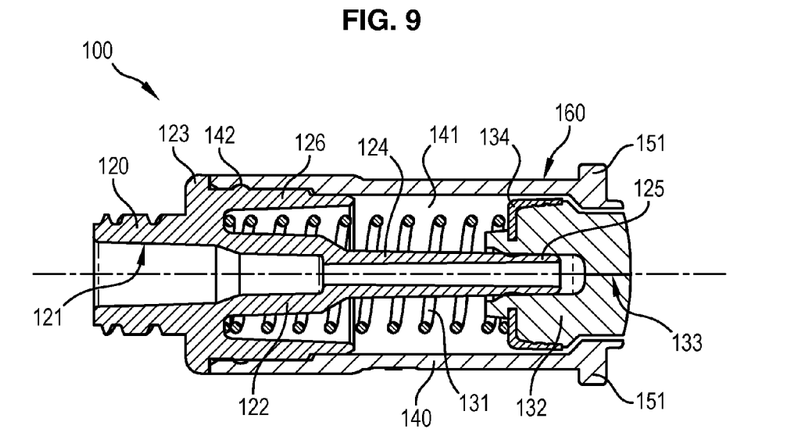
FIG. 9 is a sectional view of a third embodiment of a sectional view of a set of connectors comprising female locking means according to the invention.

The bayonet locking means respond especially to this definition, and are therefore covered by the invention, by clipping (i.e. by deformation elastic of a holding element projecting from the surface of the distal part of one of the locking means, then penetration into a complementary orifice provided in the surface of the distal part of the other of the locking means, see for example FIG. 9), etc.

In the case of bayonet locking means, the holding means 151 of the male locking means comprise at least one pin extending transversally to the exterior from the external smooth surface 160. The holding means 151 preferably comprise two pins, extending on either side of the distal coupler 140 of the female connector 100.

Each pin 151 can have a circular, square, elliptical, or any other cross-section adapted to effectively keep the female connector 100 in position relative to the male connector 200.

The holding means of the female locking means 250 as such comprise at least one groove 252 formed in a surface 260 of a collar 251. The groove 252 can be continuous to form a slot as illustrated in the attached figures, or blind.

The collar 251 is made of material with the casing 220. By way of variant embodiment, it is attached to the casing, for example by adhesion or welding or by any other means enabling such assembly. Illustrated here, the collar 251 is in the form of a tube attached at the level of a proximal end by grooves 260 to the casing 220. Passages 261 are consequently made between the grooves 261. Here, there are four grooves 260 and uniformly distributed over a circumference of the collar 251. As a consequence, there are also four passages and uniformly distributed over said circumference of the collar 251. Such a structure allows optimal cleaning of the collar and therefore of the male connector 200.

The female locking means 250 preferably comprises at least as many grooves 252 as there are pins 151 on the male locking means 150.

Each groove 252 preferably has a free end terminating on a distal end of the collar 251, the other end being closed and provided to form a longitudinal stop for the pin 151.

Figure 5A:
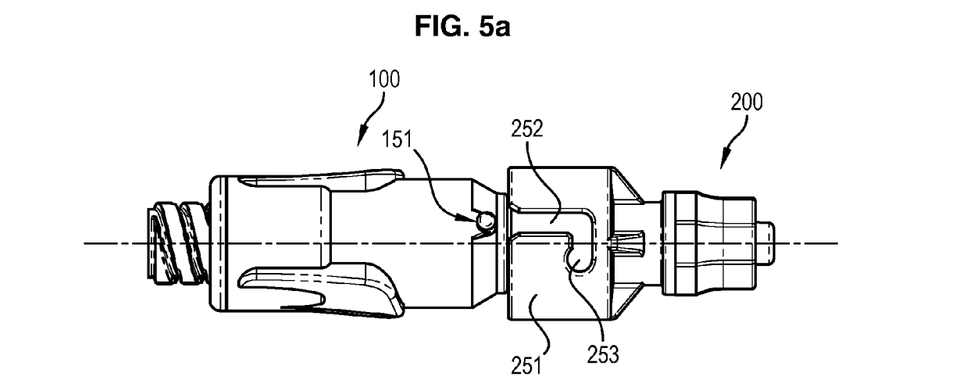
FIG. 5a is a side elevation of a set of connectors according to the invention corresponding to FIGS. 3a and 4a, put in contact.

Also, the grooves 252 are arranged on the collar 251 such that their respective free end is opposite a pin 151 when the distal ends 140, 240 of the male 200 and female 100 connectors are put in contact prior to connection, as illustrated in FIG. 5.

In this way, during connection of the male 200 and female 100 connectors, each pin 151 of the male locking means 150 penetrates respectively into a groove 252 of the female locking means 250.

By way of variant (illustrated in FIGS. 3b and 4b), the central part 270 of the distal coupler, enclosed by the collar, is threaded so as to constitute a connectable entry of female Luer-Lock type. For this, the distal part of the collar 251 is shortened such that the face of the central part 270 is accessible radially. The result is female locking means which can be connected either to male locking means 150 such as those described in reference to FIG. 2, or to locking means of complementary male "Luer-Lock" type.

The interest in this embodiment is that it especially enables connection of the connector 200 with an injector comprising locking means of Luer-Lock type.

This embodiment also has the advantage of being easy to clean to the extent where the internal surface 260 of the collar 251 and the external surface 160 comprising the pins 151 are smooth, whereas the central threaded part 270 is accessible directly by a manipulator for cleaning it.

In another variant, (not shown in the figures), the female locking means can comprise a collar comprising at least one pin projecting from its internal surface, complementary to male locking means comprising an external smooth surface in which a groove (discontinuous) is formed.

Advantageously, these embodiments ensure the operator that the male 200 and female 100 connectors are effectively properly connected.

In fact, the operator can verify visually and mechanically if the pin 151 is right at the bottom of the groove 252, which implies that the tubes 124 and 215 are effectively properly connected, as opposed to conventional connectors comprising threaded locking means which disallow such verification.

The length of a groove 252 is preferably at least equal to the relative maximal distance travelled by the connectors 100, 200 when they are connected by an operator. This relative distance will also be detailed hereinbelow.

The width of a groove 252 is substantially equal to the diameter of the corresponding pin 151, taken in the direction transversal to the direction of insertion of the pin 151 in the groove 252. In this way, the pin 151 can shift longitudinally in the groove 252 while being blocked transversally during its insertion in the groove 252.

If needed, the groove 252 is also shaped bent so that it can hold the fixed pin 151 longitudinally when the latter arrives at a stop. For example, the groove 252 has a longitudinal part 252a, in length at least equal to the relative distance travelled by the connectors 100, 200 during their connection, and a transversal part 252b extending in a direction substantially perpendicular to the direction of insertion of the pins 151.

By way of variant, the angle formed between the transversal part 252b and the longitudinal part 252a of the groove 252 is acute so as to accentuate the holding of the pin 151 and therefore the locking of the set of connectors 100, 200.

However, irrespective of the embodiment, the grooves 252 formed in a given collar 251 are identical. In particular, they have an identical size, shape and orientation so that the pins 151 can easily penetrate the groove 252 to which they are linked.

By way of variant, the associated grooves 252 and pins 151 can be of different width in pairs, so that a given pin 151 (having a given transversal diameter) may not penetrate a groove 252 having a lesser width, ensuring an undeceiving function.

According to an embodiment, the closed end of each groove 252 is also provided with a recess or seat 253 positioned in the end of the groove 252 acting as stop for the pin 151. Where necessary, the recess 253 is offset relative to the axis of the groove 252 to transversally block the pin 151 in the groove 252, and therefore further improve the locking of the set of connectors 100, 200. For example, when the groove 252 is bent, as illustrated especially in FIGS. 4 and 5, the recess 253 is placed in the closed end of the transversal part 252b of the groove 252 and is offset in the direction of the distal end relative to the axis of said transversal part 252.

In reference to FIGS. 5a-5b to 7, the interactions of the different elements described hereinabove will now be described.

Figure 5B:
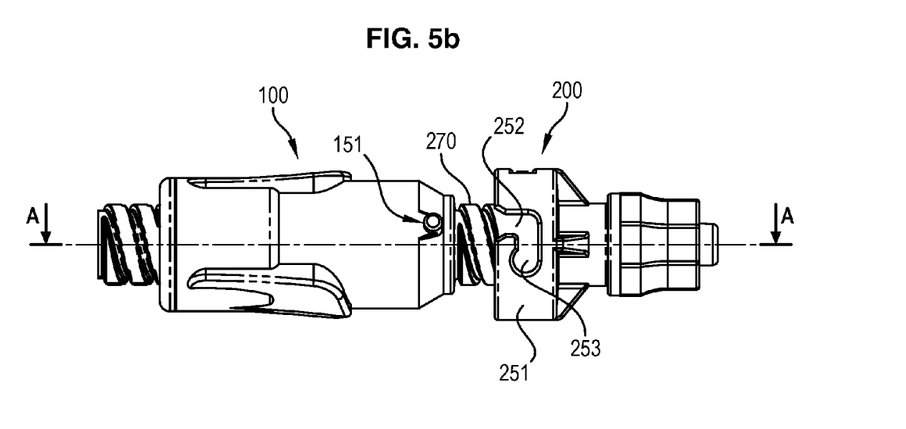
FIG. 5b is a side elevation of a set of connectors according to the invention corresponding to FIGS. 3b and 4b, put in contact.
Figure 6:
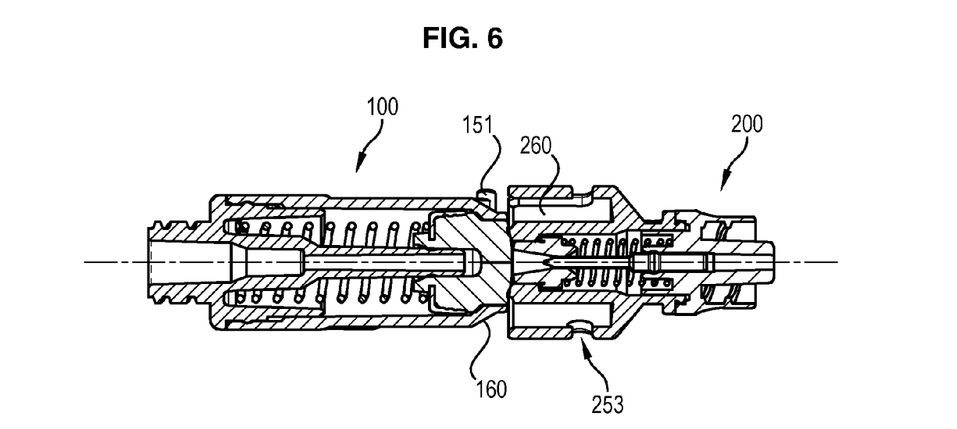
Figure 7:
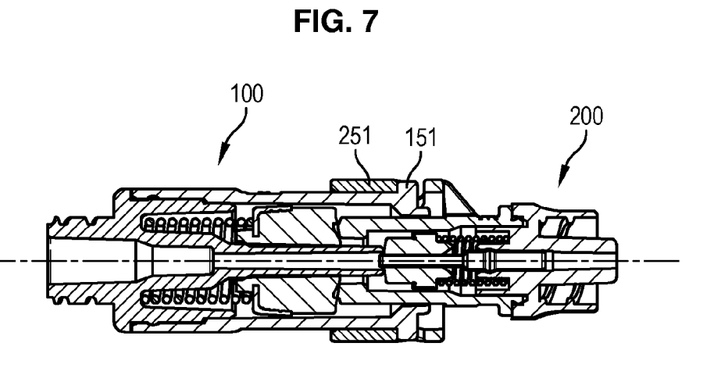
FIG. 7 is a sectional view of the set of FIG. 5a, when the connectors are locked together.
Figure 8:
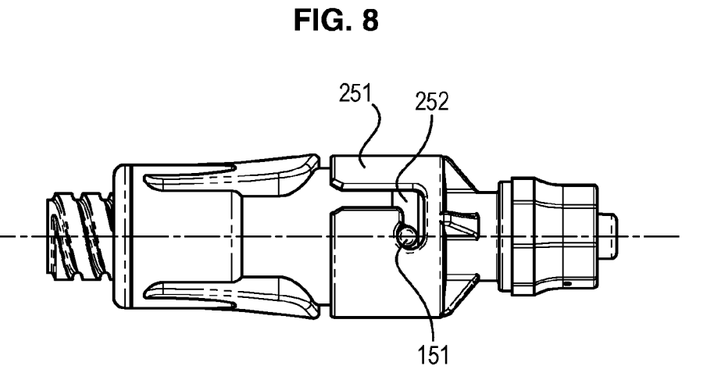
FIG. 8 is a side elevation of the set of FIG. 7.

FIGS. 5a, 5b and 6 represent female 100 and male 200 connectors in a stable downstream blocking position. In this position, the membranes 130, 230, tightly blocks the passages 141, 211, such that downstream surfaces of the membranes 130, 230, are flush with the downstream ends of said passages.

For information, in this position, a manipulator of the connector 100, 200 can easily clean said downstream surface of the membrane to reduce the risk of nosocomial infections which could result in poor cleaning or difficult cleaning of this surface.

Because of locking means 150, 250 and the structure of the male 200 and female 100 connectors according to the invention, counterpressure sealing is strongly increased without destroying performance in terms of repeated connections/disconnections. Also, the use of rigid cups 134, 234 prevents any expulsion of the septums 130, 230 outside the connectors 100, 200 according to the invention under the effect of strong pressure.

During initial use, the operator cleans the distal end of the membranes 130, 230 to remove any presence of germs or bacteria, as well as the bayonet locking means 150, 250 (and where required the central part 270).

It should also be noted that replacing conventional threadings by the bayonet locking means 150, 250 (and where required the central part 270) according to the invention greatly eases this cleaning.

Once cleaning is complete, the operator puts in contact the respective septums of the male connector 200 and of the female connector 100, as is illustrated in FIG. 5a,5b, then connects the set. This connection between the connector 100 and the connector 200 is done by locking the pins 151 of the distal coupler 140 of the female connector 100 in the corresponding grooves 252 of the distal coupler 240 of the male connector 200.

It is remarkable that, as the distal couplers 140 and 240 of the two female 100 and male 200 connectors are structurally similar (naturally outside their respective locking means), their respective membranes 130, 230 are flush at the level of the distal end of their distal coupler 140, 240. In this way, the coupling/uncoupling of the male connector 200 and of the female connector 100 is completed in a single axial movement only. In fact it is no longer necessary to fix the distal couplers 140, 240 of the female 100 and male 200 connectors before starting to push the connectors towards each other, these two operations being performed simultaneously on the one hand due to the structure of the distal couplers 140, 240 and on the other hand to the locking means according to the invention.

More precisely, the operator places the pins 151 of the female connector 100 opposite the corresponding grooves 252, then slides the connectors 100, 200 relatively one relative to the other by pushing the female connector 100, supported on the handling means 143 of the distal coupler 140, towards the male connector 200.

During this handling the distal end of the male connector 200 pushes on the distal end of the membrane 130 of the female connector 100, which on the one hand stresses the membrane body 131 to compress, and on the other hand forces the distal end 125 of the hollow tube 124 to pass through, by means of the slot 133, the membrane thickness located at the distal end of the membrane 130.

Once the distal end 125 of the tube 124 has passed through the membrane thickness of the distal end of the membrane 130, this distal end 125 of the tube 124 comes in supported contact with the septum 230 of the connector 200. The distal end 125 of the tube 124 then pushes the septum 230, on the one hand, against the underlying spring 231 and, on the other hand, against the tube 214 which passes through the septum 230 via the slot 233 which is made in it.

The thrust continues until the distal end 125 of the tube 124 of the female connector 100 receives the distal end of the tube 214 of the male connector 200. Therefore the connection and a liquid passage are made between the male 200 and female 100 connectors.

The relative distance travelled by the connectors 100, 200 during handling is defined by the length of the longitudinal part 252a of the grooves 252. In this final position, in which the connectors 100, 200 are connected and in fluidic communication, the pins 151 are therefore stopped at the bottom of the longitudinal part 252a of the grooves 252.

The operator rotates the connectors 100, 200 one relative to the other so as to position the pins 151 in the closed end of the transversal part 252b of the grooves 252 until they reach their siege 253 and locks the set of connectors 100, 200.

On disconnection, the operator rotates the connectors 100, 200 one relative to the other in the direction opposite that of locking to withdraw the pins 151 from the transversal part 252b of the grooves 252, then takes away the connectors 100, 200 by means of the thrust of the two springs. The pins 151 exit from the longitudinal part 252a of the grooves 252, the membranes 130, 230 again progressively cover the tube 124, 214 respectively tightly and the membranes 130, 230 now tightly block the respective distal ends of the connectors 100, 200.

During connection or disconnection, sealing is assured throughout operation. In fact, sealing is first assured by contact of the distal end of the membrane 130 on the septum 230, then by contact of the distal end 125 of the hollow tube 124 on the septum 230 of the male connector 200—said contact being maintained by the locking of the set of connectors—and finally by insertion of the tube 214 into the hollow tube 125.

Numerous modifications can of course be made to the invention without departing from the scope of the latter.

The invention claimed is:

1. A secure connector set for a liquid circuit, comprising: a male connector and a female connector, each comprising a proximal coupler and a distal coupler, wherein the distal coupler of each of the male and female connectors defines a passage and comprises: a tubular part; a connection element mounted and fixed on the proximal coupler and extending coaxially in the tubular part; and an elastically deformable membrane, substantially tubular, closed at a distal end by a membrane thickness, wherein the elastically deformable membrane of the male connector is mobile between a downstream blocking position, in which the elastically deformable membrane of the male connector tightly covers a free end of the connection element of the male connector, and an upstream connection position, in which the connection element of the male connector passes through the elastically deformable membrane of the male connector, the male connector comprising a first elastic means configured to be supported on the proximal coupler of the male connector and to thrust the elastically deformable membrane of the male connector into the downstream blocking position, wherein the elastically deformable membrane of the female connector is mobile between a downstream blocking position, in which the elastically deformable membrane of the female connector tightly covers a free end of the connection element of the female connector, and an upstream connection position, in which the connection element of the female connector passes through the elastically deformable membrane of the female connector, the female connector comprising a second elastic means configured to bear on the proximal coupler of the female connector and to thrust the elastically deformable membrane of the female connector into the downstream blocking position, wherein the tubular part of the distal coupler of the male connector is adapted to be inserted, during connection, into the tubular part of the distal coupler of the female connector, and wherein, in a downstream blocking position, for each of the male and female connectors, the elastically deformable membrane of the male connector is encapsulated in the tubular part of the distal coupler of the male connector and sealingly blocks the passage of the distal coupler of the male connector and is flush with the distal end of the distal coupler of the male connector, and wherein, in a downstream blocking position, for the female connector, the elastically deformable membrane of the female connector is encapsulated in the tubular part of the distal coupler of the female connector and sealingly blocks the passage of the distal coupler of the female connector and is flush with the distal end of the distal coupler of the female connector.

2. The connector set as claimed in claim 1, wherein an external surface of the tubular part of the female connector is devoid of threading.

3. The connector set as claimed in claim 1, wherein an external surface of the tubular part of the male connector comprises threading so as to constitute a connectable entry of "Luer-Lock" type.

4. The connector set as claimed in claim 1, wherein the connection element of the male connector and the connection element of the female connector are hollow tubes, and
wherein the hollow tube of the male connector is adapted to be inserted into the hollow tube of the female connector.

5. The connector set as claimed in claim 1, wherein an external surface of the tubular part of the distal coupler of the male connector and of the female connector is smooth and has an unvarying axial cross-section over a substantially continuous part and comprises holding means extending transversally, said external surface and said holding means together forming male or female locking means.

6. The connector set as claimed in claim 5, wherein the holding means of the male locking means comprises at least one pin extending transversally from the external surface relative to the longitudinal direction of the distal coupler comprising the male locking means.

7. The connector set as claimed in claim 5, wherein the male locking means comprises two pins extending on either side of the distal coupler comprising the male locking means, in opposite directions.

8. The connector set as claimed in claim 5, wherein the female locking means comprises at least one groove formed in a surface of a collar and configured to receive a pin of the male locking means.

9. The connector set as claimed in claim 8, wherein the groove is bent at an angle.

10. The connector set as claimed in claim 9, wherein the collar extends over part of the distal coupler comprising the female locking means only.

11. The set as claimed in claim 10, wherein an external surface of the tubular part of the male connector comprises threading so as to constitute a connectable entry of "Luer-Lock" type, and the threading extend on the surface of the tubular part not covered by the collar.

12. The connector set as claimed in claim 9, wherein the collar is open-work at the level of a proximal end.

13. The connector set as claimed in claim 1, wherein the membrane of the male connector comprises a slot in the membrane thickness arranged so as to be traversed by the connection element of the male connector in an upstream connection position, and
wherein the membrane of the female connector comprises a slot in the membrane thickness arranged so as to be traversed by the connection element of the female connector in an upstream connection position.

14. A method for securing a secure connector set as claimed in claim 1, comprising:
cleaning the membrane of the male connector and the membrane of the female connector;
putting in place the proximal couplers of the male connector and the female connector such that their respective membranes are in contact and the male connector and the female connector have their longitudinal axes joined to create a tight seal of the male connector and the female connector;
inserting the male connector into the female connector such that the connection element of the male connector is connected in the connection element of the female connector, the connection element of the female connector passing through the membrane of the female connector; and
locking the male connector and the female connector.

* * * * *